(12) United States Patent
Bouwman et al.

(10) Patent No.: US 9,045,410 B2
(45) Date of Patent: Jun. 2, 2015

(54) NICKEL HYDROGENATION CATALYST

(71) Applicant: BASF Corporation, Florham Park, NJ (US)

(72) Inventors: Hermanus Johannes Bouwman, De Meern (NL); Robert Johan Andreas Maria Terörde, De Meern (NL); Tjalling Rekker, De Meern (NL)

(73) Assignee: BASF CORPORATION, Florham Park, NJ (US)

( * ) Notice: Subject to any disclaimer, the term of this patent is extended or adjusted under 35 U.S.C. 154(b) by 0 days.

(21) Appl. No.: 14/350,889

(22) PCT Filed: Oct. 12, 2012

(86) PCT No.: PCT/IB2012/055550
§ 371 (c)(1),
(2) Date: Apr. 10, 2014

(87) PCT Pub. No.: WO2013/054303
PCT Pub. Date: Apr. 18, 2013

(65) Prior Publication Data
US 2014/0256972 A1    Sep. 11, 2014

(30) Foreign Application Priority Data

Oct. 12, 2011  (EP) ..................................... 11184937

(51) Int. Cl.
| C07C 51/36 | (2006.01) |
| B01J 37/03 | (2006.01) |
| B01J 21/08 | (2006.01) |
| B01J 23/755 | (2006.01) |

(Continued)

(52) U.S. Cl.
CPC ................. C07C 51/36 (2013.01); B01J 37/03 (2013.01); B01J 21/08 (2013.01); B01J 23/755 (2013.01); B01J 35/10 (2013.01); C11C 3/123 (2013.01); C07C 5/02 (2013.01)

(58) Field of Classification Search
CPC ............ C11C 3/12; C11C 3/00; C11C 3/123; C01B 2203/1052
USPC ........................................................ 554/141
See application file for complete search history.

(56) References Cited

U.S. PATENT DOCUMENTS 5,258,346 A * 11/1993 Huang et al. ................... 502/259

FOREIGN PATENT DOCUMENTS

DE           1561 87        4/1982
DE           156187 A1 *    8/1982
(Continued)

OTHER PUBLICATIONS

Yuriko Nitta: "Preparation Chemislry of Precipitated Ni—SiO2 Catalysts for Enantioselective Hydrogenation", Journal of Catalysis, Jan. 1, 1985, pp. 429-438.*

(Continued)

*Primary Examiner* — Deborah D Carr
(74) *Attorney, Agent, or Firm* — Elizabeth Pietrowski

(57) ABSTRACT

The invention relates to a catalyst comprising nickel and a solid silica support, to a process for preparing such a catalyst and to a process for the hydrogenation of an unsaturated fatty material. According to the invention there is provided a catalyst comprising nickel on a solid silica support, wherein said catalyst has a specific pore volume of at least 0.4 ml/g and a TPR peak maximum within the range of 360-420° C.

16 Claims, 3 Drawing Sheets

Figure 1:
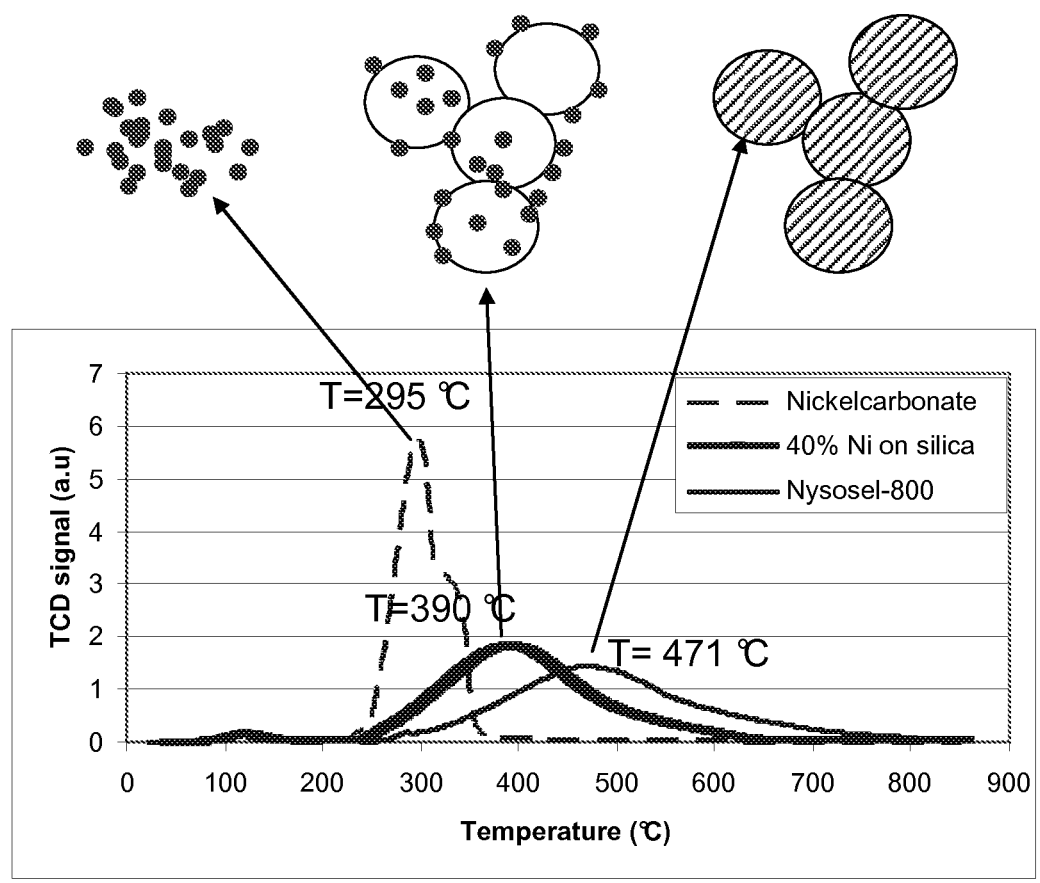

(51) Int. Cl.
*B01J 35/10* (2006.01)
*C11C 3/12* (2006.01)
*C07C 5/02* (2006.01)

(56) References Cited

FOREIGN PATENT DOCUMENTS

WO  02/07880 A1  1/2002
WO  WO 0207880 A1 * 1/2002

OTHER PUBLICATIONS

Yuriko Nitta, Toshinobu Imanaka, and Shiichiro Teranishi, Preparation Chemistry of Precipitated Ni—SiO2 Catalysts for Enantioselective Hydrogenation; Journal of Catalysis 96, 429-438 (1985).

* cited by examiner

NICKEL HYDROGENATION CATALYST

CROSS REFERENCE TO RELATED APPLICATIONS

This application claims priority from PCT/IB2012/055550 having a priority date of Oct. 12, 2011 based on EP 11184937.8, all of which are incorporated herein by reference in its entirety.

The invention relates to a catalyst comprising nickel and a solid silica support, to a process for preparing such a catalyst and to a process for the hydrogenation of an unsaturated fatty material.

It is known to prepare partially hydrogenated unsaturated fatty materials, such as oils or fatty acids, and especially edible oils, such as soybean oil, rapeseed oil, palm oil, canola or fish oil, by catalytic hydrogenation in the presence of hydrogen. Hydrogenation can take place utilizing conventional hydrogenation catalysts, such as nickel or precious metal catalysts.

Catalysts suitable to be used in the hydrogenation of edible oil preferably have a small particle size, large pores, high catalytic metal dispersion and excellent filtration properties.

Nickel powder catalysts, coated with fat (droplets) to prevent oxidation, are often used for oils and fatty acids hydrogenation reactions. Such catalysts typically contain between 16 and 25 wt. % Ni, calculated on the weight of the droplets including the coated catalyst. A nickel powder catalyst is typically prepared by co-precipitation of nickel and a soluble support, where the amount of Ni loaded onto the support is typically about 60 wt. %, based on the weight of the calcined catalyst. A commercially obtainable example is Nysosel™ 800 catalyst.

EP-A-0 114 704 describes a process for preparing a nickel-based catalyst comprising precipitation of nickel hydroxide/carbonate, followed by an ageing step lasting between 20 to 180 minutes and at a temperature between 60 and 100 ° C. EP-A-0 114 704 also describes that the catalyst produced comprises aggregates of nickel/nickel compounds and that these aggregates have an outer surface which is at least 60% free of carrier particles attached thereto.

A disadvantage of the co-precipitation method is that important catalyst characteristics such as particle size and specific pore volume can only be controlled to a limited degree. The high nickel loadings used also disadvantageously limit metal dispersion in the catalyst. The co-precipitation method and the precipitation method described in EP-A-0 114 704 also results in the formation of nickel silicate. This is undesirable because nickel silicate is difficult to reduce, requiring the use of high reduction temperatures and results in a loss of metal dispersion.

WO-A-02/07880 describes a nickel/silica hydrogenation catalyst which comprises nickel silicate as an essential component. The disadvantage of this catalyst is that the presence of nickel silicate limits the total amount of nickel in the catalyst that can be readily reduced.

U.S. Pat. No. 5,258,346 describes a nickel hydrogenation catalyst prepared by precipitating a solution of nickel nitrate by addition of sodium carbonate onto amorphous silica at about 90° C., followed by an aging step lasting three hours at this temperature. The disadvantage of this method is that it also results in the formation of nickel silicate which limits the total amount of nickel in the catalyst that can be readily reduced.

DD-A-1 561 87 describes a process for preparing a nickel catalyst by precipitating a concentrated solution of nickel nitrate using sodium carbonate onto silica. The disadvantage of using such a concentrated nickel nitrate solution is that is leads to high nickel loadings which limit metal dispersion in the catalyst.

Nitta et al. (Journal of Catalysis 96(1985)429-438) the preparation of Ni-silica catalysts by precipitating nickel nitrate solutions suspended in silica gel using sodium carbonate using high nickel loadings as well as high precipitation temperatures. Again, the high nickel loadings used disadvantageously limit metal dispersion in the catalyst. Again, the high precipitation temperatures result in formation of nickel silicate which limits the amount nickel in the catalyst that can be readily reduced.

It is an object of the present invention to provide a new nickel catalyst for the hydrogenation of unsaturated fatty material that enables markedly reducing the nickel content calculated on the weight of the coated catalyst, while maintaining the same activity on (equal) catalyst weight base of the coated catalyst.

It has been found that this object can be realized by a nickel catalyst prepared by deposition precipitation of nickel directly onto a solid silica support, resulting in a catalyst exhibiting much more activity for the hydrogenation reaction in unsaturated fatty material feedstocks. In particular, it has been found that such a catalyst has a higher activity per equivalent of nickel than known nickel catalysts.

Accordingly, the present invention relates to a catalyst comprising nickel on a solid silica support wherein said catalyst has a specific pore volume ($N_2$, 20-600 Å) of at least 0.4 ml/g and having a TPR peak maximum at the temperature between 360-420° C. Without wishing to be bound by theory, it is believed that the nickel particles are essentially directly deposited onto the silica surface, i.e. without any substantial formation of nickel salts, such as nickel silicates or nickel hydrosilicates.

Preferably the catalyst of the present invention comprises 20-48 wt. %, nickel, preferably 30-45 wt. %. Unless indicated otherwise, nickel contents are expressed herein as metallic nickel on the weight of the calcined catalyst.

The advantage of the catalyst of the present invention is the lower nickel content that allows for higher nickel dispersion in the catalyst. In contrast, known nickel catalysts with higher nickel contents are unable to achieve such a high dispersion of nickel in the catalyst. A further advantage of the catalyst is that >90 wt. %, preferably >95 wt. %, more preferably 96-99 wt. %, even more preferably 97-98 wt. % of the nickel is present in the metallic form following reduction. This is much higher than commercial nickel catalysts where only about 70% of the nickel is in the reduced metallic form.

For a good activity, the specific pore volume for the unreduced catalyst precursor is at least 0.4 ml/g, preferably at least 0.5 ml/g, more preferably at least 0.55 ml/g. Unless explicitly indicated otherwise, all specific pore volumes expressed herein are measured on a Quantachrome™ Autosorb™ 6 by $N_2$ desorption in the pore range of 20-600 Å on samples that are calcined during 1.5 hours at 375° C.

The upper limit is not particularly critical. Very good results have been achieved with specific pore volumes up to 0.75 ml/g.

The temperature programmed reduction (TPR) peak maximum of the catalyst of the present invention is between 360-420° C. TPR is a well known technique for the characterization of heterogeneous catalysts to find the most efficient reduction conditions and comprises an oxidized catalyst precursor being submitted to a programmed temperature rise while a reducing gas mixture is flowed over it.

A simple container (typically a U-tube) is filled with a solid or catalyst. This sample vessel is positioned in a furnace with temperature control equipment. A thermocouple is placed in the solid for temperature measurement. To remove the present air the container is filled with an inert gas. Flow controllers are used to add hydrogen in an argon mixture. The composition of the gaseous mixture is measured at the exit of the sample container with appropriate detectors. The sample in the furnace is heated up on predefined values. If a reduction takes place at a certain temperature, hydrogen is consumed which is recorded by e.g. thermal conductivity detector (TCD). Such TCD signal is then converted to concentration of active gas using a level calibration. Unless indicated otherwise, in the present description and claims, the above protocol is used to measure the TPR peaks of calcined materials (at 375° C. during 1.5 hours) of the present invention, using the following specific settings: concentration of $H_2$ in Ar: 15%, ramp rate: 5° C./min, gas flow: 20 ml/min, and sample size: 0.1 gram.

FIG. 1 shows TPR profiles for (i) a commercial catalyst Nysosel-800 (thin solid line), (ii) nickel carbonate (dashed lines) and (iii) a catalyst of the present invention with 40 wt. % Ni on silica, based on the weight of the calcined catalyst (thick solid line). This figure illustrates TPR spectra. The peak maximum indicates the temperature that corresponds to the maximum rate of reduction. As shown in FIG. 1, the TPR peak maximum for the catalyst of the present invention (iii) is 390° C., which is midway between the TPR peak maximum of the typical co-precipitated catalyst, e.g. comparative sample (i) (471° C.), and the TPR peak maximum of the unsupported nickel carbonate (ii) (295° C.).

The catalyst of the present invention comprises substantially no nickel silicate. This is advantageous because more of the nickel in the catalyst is present in the active form.

Figure 2:
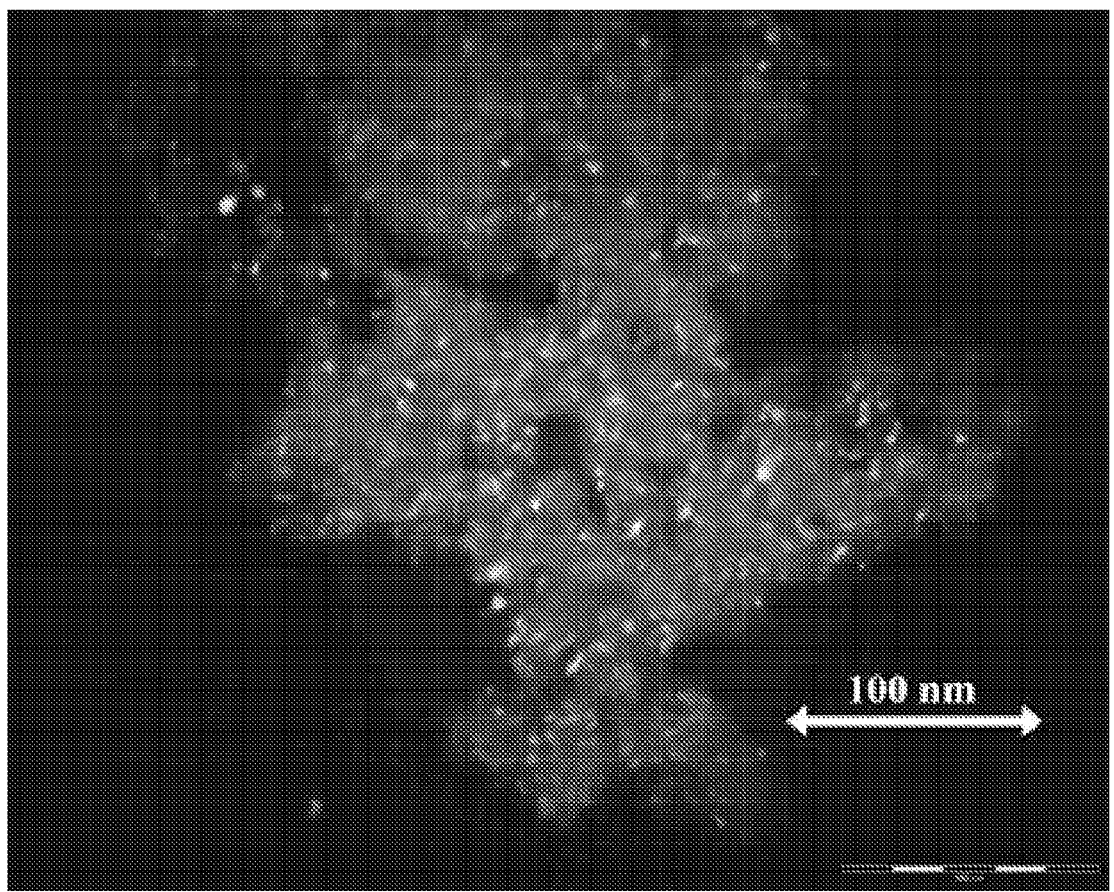

FIG. 2 shows a transmission electron microscopy (TEM) image of a catalyst according to the present invention comprising 45 wt. % Ni on silica based on the weight of the calcined catalyst. This TEM image was taken in darkfield (175000×).

Optionally the catalyst further comprises a catalyst promoter. Suitable promoters are selected from the group consisting of alkaline earth metals, manganese and combinations thereof. The alkaline earth metals are Group 2 metals from the periodic table and include beryllium, magnesium, calcium, strontium, barium and radium. Preferably the promoter is present in an amount of between 1 to 10 wt. %, more preferably 1-5 wt. %. Unless indicated otherwise, the promoter content is expressed herein as metallic oxide on the weight of the calcined catalyst. Preferably, the catalyst promoter is magnesium.

The catalyst of the present invention may be coated with a protective layer, e.g. a fatty substance such as hardened soy bean fat, hardened palm oil fat, hardened sun flower oil fat or combinations thereof, which may serve to avoid oxidation of (parts of) the catalyst. A method for applying a suitable fatty substance is generally known in the art, and may be based on WO-A-2004/035204 which is incorporated herein by reference. This may for example be done by blending a (reduced) catalyst powder into the molten coating material (such as the molten fat) and subsequently solidifying the resulting suspension to form flakes or droplets of coated catalyst particles.

The melting temperature of the protective material with which the catalyst is coated is preferably less than the temperature at which the hydrogenation is carried out, in order to facilitate dissolution of the protective material at the beginning of a hydrogenation process. In particular, when the catalyst is used in a slurry process, the protective coating will preferably dissolve in the feedstock. Else, the coating may be removed from the process, shortly before using the catalyst in a hydrogenation process. The coating may very suitably be removed by contacting the catalyst with a solvent, such as a feedstock, preferably at a temperature higher than the melting point of the coating fat.

The catalyst of the invention may be in the form of a catalyst suspended in droplets, wherein the droplets form a protective coating layer effective in preventing oxidation of the catalyst, wherein said protective coating layer preferably comprises a fatty substance. A droplet according to the present invention typically comprises the reduced catalyst coated in a fatty substance, wherein said droplet comprises about 9-13 wt. % nickel, calculated as metallic nickel, about 9-26 wt. % $SiO_2$, optionally about 0.5-1 wt. % of a promoter calculated as metallic oxide, and the balance of the droplet is the fatty substance. The particle size distribution of the catalyst of the present invention, in particular the volume mean diameter D(v0.5), wherein D(v0.5) is the diameter where 50% of the distribution is above and 50% is below, is preferably between 2-10 µm, more preferably between 3-8 µm and most preferably between 4-6 µm. D(v0.5), as used herein, is the value as measured by laser diffraction with a Malvern MS 2000 system and sampling unit Hydro 2000G, which corresponds to a measuring range of 0.02-2000 µm using the "General purpose" as the model for calculating the particle size. The D(v0.5), as used herein, is the volume mean diameter of the unreduced catalyst per se, i.e. without a protective coating. Alternatively these particles may be shaped (extruded, tabletted, etc.) into larger particles, especially suitable for fixed bed applications. Such applications may include, in addition to the hydrogenation of unsaturated fatty materials, such as oils or fatty acids, and especially edible oils, the dearomatization, desulfurization and hydrogenation of petrochemical feedstocks and functional groups such as aldehydes and nitro groups. For feedstocks containing a high level of sulfur contamination, the catalyst may be mixed or promoted with metal oxides that form stable metal sulfides as described in WO-A-2005/028403 and U.S. Pat. No. 5,482,616, which are incorporated herein by reference. Suitable metal oxides described in U.S. Pat. No. 5,482,616 include oxides of inter alia silver, lanthanum, antimony, nickel, bismuth, cadmium, lead, tin, vanadium, calcium, strontium, barium, cobalt, copper, tungsten, zinc, molybdenum, manganese and iron. Preferably the metal oxide is zinc.

The nickel surface area of the catalyst (in active form) will preferably have hydrogen adsorption capacity (HAC) ranging from 50-90 ml $H_2$/g Ni. The nickel surface area as used herein is the value that can be determined as follows. Hydrogen desorption is performed on a sample of 0.1 g in a Micromeretics AutoChem 2920 chemisorption analyzer, after in situ reduction with hydrogen (50 ml/min) for 2 hours at 400° C. Following in situ reduction, the sample is cooled to −75° C. with liquid nitrogen. Subsequently, the hydrogen adsorption capacity (HAC) of the sample is determined by measuring the amount of hydrogen that desorbs during heating in a flow of argon (20 ml/min) from −75 to 700° C.

The BET surface area is typically between 160 to 300 m²/g, preferably between 180 to 280 m²/g, and more preferably between 200-280 m²/g. The BET surface area as used herein is the value that can be measured by determining the amount of nitrogen adsorbed at 77 K and $P/P_0$ of approximately 0.3 and assuming a nitrogen cross sectional area of 16.2 Å², after degassing the catalyst sample at 180° C.

Figure 3:
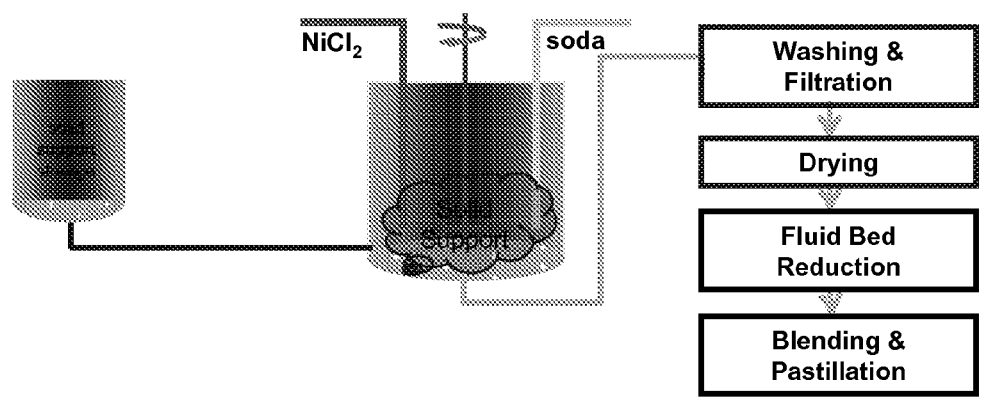

In a preferred embodiment, the catalyst is made from a catalyst precursor that is prepared by deposition-precipitation. In a deposition-precipitation process according to the process of the present invention nickel is precipitated onto a solid silica support that is suspended in the reactor vessel. In such a process, a nickel source may be mixed in a liquid (e.g. water or an aqueous solution) in which the slurried support is suspended, to form a precipitate (a catalyst precursor), comprising all said components, by adding a precipitant, such as an alkaline compound at some stage. FIG. 3 illustrates the deposition precipitation process of present invention.

Optionally one or more catalyst promoters are precipitated together with nickel (i.e. without forming intermediate precipitates of only one or some of the components) onto the solid silica support that is suspended in the reactor vessel.

Suitable nickel sources include metal salts such as the nitrates, acetates, sulfates, chlorides, etc., most preferably chlorides. Preferably the metal source is a solution of any of these salts.

Suitable solid silica sources include precipitated silica and diatomaceous earth (kieselguhr). Preferably the silica source is a suspension of any of these components. The silica sources suitable to be used are highly porous and have a specific pore volume of about 0.4-2 ml/g, preferably about 1.6-1.8 ml/g.

Suitable catalyst promoter sources are metal salts, such as the nitrates, acetates, sulfates, chlorides, or combinations thereof.

Suitable precipitants to initiate precipitation include alkaline compounds, e.g. an alkali metal carbonate (such as $Na_2CO_3$) or an alkali metal hydroxide (such as NaOH).

It is an advantage of the above deposition precipitation methodology that it can be performed in a single deposition precipitation step.

Very good results have been achieved with a process wherein the deposition-precipitation is performed at a pH between 7.0-8.0 (as measured at the precipitation temperature). It has been found that under these conditions a very efficient, generally a substantially complete precipitation of nickel and optionally one or more catalyst promoters, can be realized, in particular at precipitation temperatures of <70° C., preferably <65° C. and more preferably ≤60° C. The lower temperatures are preferred, because it was found that the reaction between nickel and the support is suppressed at lower temperature.

Figure 4:
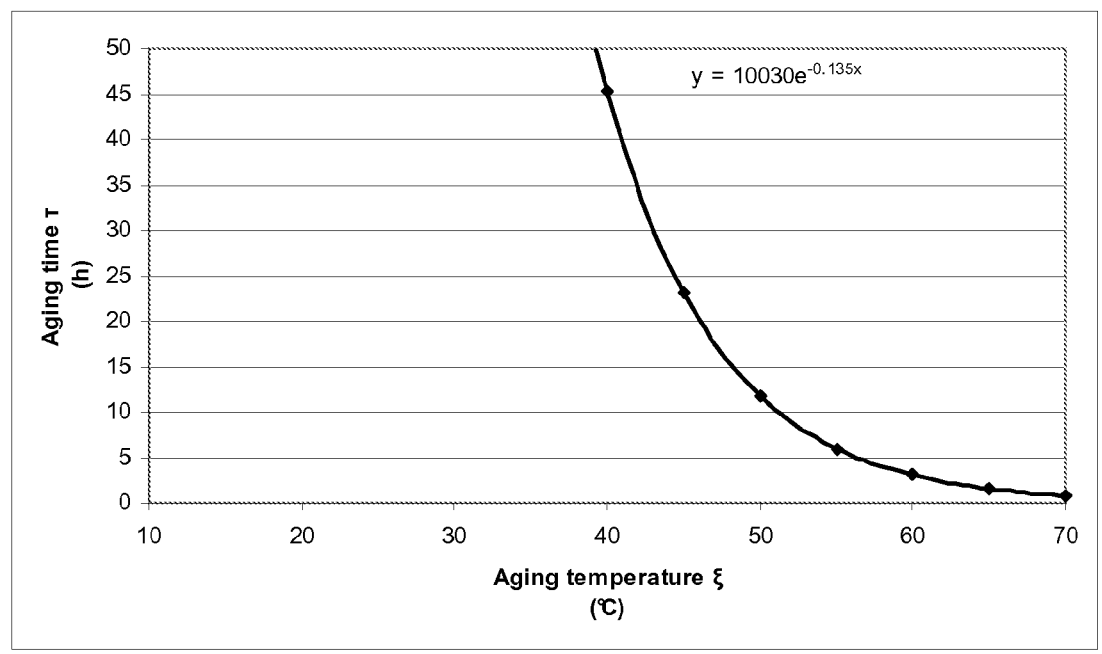

Following the precipitation reaction, the catalyst precursor is brought to a temperature of ≤50° C., optionally by cooling. Preferably the temperature of the catalyst precursor is brought down to room temperature. Optionally, the catalyst precursor is aged prior to bringing the temperature ≤50° C. The maximum aging time is dependent on the aging temperature and preferably follows the expression $\tau << 10030 \times e^{(-0.135 \times \xi)}$, wherein $\tau$ is the aging time in hours and $\xi$ is the aging temperature in ° C. This relation is also shown in FIG. 4. As can be seen from FIG. 4, higher aging temperatures result in shorter aging times.

The catalyst precursor may thereafter be isolated, e.g. by filtration, from the liquid solution and dried. Preferably the catalyst precursor may be calcined before being reduced. The catalyst may very suitably be activated by reduction with hydrogen, e.g. at a temperature between 350-450° C., e.g. for 1-5 hours.

The advantage of deposition precipitation of nickel onto a solid silica support in accordance with the present invention is that it allows selection of a suitable silica support and optimization of pore structure and particle size distribution. A further advantage is that lower Ni loadings may be used, typically about 20-48 wt. %, of nickel, preferably about 30-45 wt. %, calculated as metallic nickel on the weight of the calcined catalyst. This allows for higher Ni dispersion on the catalyst. Furthermore, less nickel silicate is formed, which enables lower reduction temperatures to be used resulting in a higher Ni dispersion on the catalyst. As a result of the minimum of metal support interaction that is needed to stabilize the nickel particles and prevent loss of dispersion during reduction, it makes maximum use of all active nickel by preventing loss into an irreducible nickel support phase.

It is believed that the nickel present in the catalyst precursor is in the form of nickel carbonate. The catalyst precursor prepared in the deposition precipitation process of the present invention, however, is very sensitive and is susceptible to losing some of its advantageous properties by further reaction of the nickel with the support. It was found that this can be maintained if the precipitation slurry is cooled down to room temperature directly after the precipitation has finished.

It was also found that substantially removing sodium, for instance to a level lower than 0.1 wt. % from the catalyst precursor, prior to drying, leads to a reduction of the further reaction of nickel with the support, which is very desirable.

It was found that during the precipitation of the catalyst precursor, the impact on the pore volume of the silica support is limited, viz. the change in specific pore volume (ml/g) of the original silica compared to the precipitated product after precipitation in accordance with the invention is smaller than with conventional precipitation processes, such as methods comprising an aging step, as illustrated in the examples hereinbelow.

In accordance with invention, the nickel may be precipitated onto a solid silica support that is suspended in the reactor vessel, wherein a nickel source may be mixed in a liquid (e.g. water or an aqueous solution) in which the support is suspended, to form a precipitate (a catalyst precursor), comprising all said components, by adding a precipitant, such as an alkaline compound at some stage.

Following the precipitation reaction, the catalyst precursor is also brought to a temperature of ≤50° C., optionally by cooling. Preferably the temperature of the catalyst precursor is brought down to room temperature.

Optionally, the catalyst precursor is also aged prior to bringing the temperature to ≤50° C. as previously discussed.

The advantage of this process of the present invention is that it allows maintenance of the large silica pores of the support and substantially prevents formation of small nickel silicate pores in the catalyst precursor. Preferably, the pore structure of the solid silica support is substantially maintained and the decrease in the pore volume is limited. Typically the decrease in specific pore volume is less than 80%, preferably less than 75%.

A catalyst according to the present invention may be used for the hydrogenation of unsaturated fatty material.

Accordingly in a preferred embodiment, the catalyst of the present invention may be employed in a process for hydrogenating an unsaturated fatty material, wherein said unsaturated fatty material is contacted with hydrogen in the presence of the catalyst.

The catalyst is preferably slurried into the unsaturated fatty material and after the hydrogenation has been completed, removed by filtration. It is also possible to use a fixed bed or loop reactor containing the catalyst in fixed form.

An important advantage of a hydrogenation process according to the present invention is the reduced amount of nickel in the catalyst required to hydrogenate the unsaturated fatty material. This provides a significant economic costs savings.

The present invention will now be illustrated by the following examples. Example 1 is a reference nickel catalyst. Examples 2-3 are nickel catalysts according to the present invention. Example 4 is a reference catalyst that is aged at a too high temperature, and as a result has a TPR peak maximum at a too high temperature.

EXAMPLE 1 (REFERENCE)

Nickel Catalyst: 59.1 wt. % Ni on Silica 1000 ml of a solution of nickel chloride (95 g/l nickel) and magnesium chloride (7.4 g magnesium per liter) in water and 1000 ml of a solution of sodium metasilicate (47.6 g/l $Na_2SiO_3.5H_2O$) and sodium carbonate (209 g per liter) were simultaneously and at the same rate pumped into a well-stirred 4-liter precipitation vessel at a temperature of 90° C. The starting volume of the water in the precipitation vessel is 1725 ml and contained 75 ml sodium aluminate solution (50.9 g/l $Al_2O_3$). The pH of the slurry was 7.5 and after about 1 hour the precipitation was completed.

After washing of the precipitate with approximately 30 liter of water, the precursor of the catalyst formed was filtered and dried in an oven at 110° C. The catalyst was activated at 400° C. with hydrogen. TPR peak maximum and the specific pore volume were determined (on calcined precursor) as 471° C. and 0.48 ml/g, respectively.

The nickel content of the reduced catalyst was 70.7 wt. %, based on the weight of the catalyst; the amount of nickel reduced was 49.3 wt. %; and the amount of nickel present in metallic form was 69.7 wt. %.

EXAMPLE 2

40 wt. % Ni on silica 1000 ml of a solution of nickel chloride (81.6 g/l nickel) in water and 848 ml sodium carbonate (220 g/l) solution were simultaneously pumped into a well-stirred 4-liter precipitation vessel at a temperature of 60° C. The starting volume of the water in the precipitation vessel was 2000 ml and contained 100 gram of highly porous silica powder, having a specific pore volume of 1.72 ml/g, a surface area of 271 m²/g and a pore peak at 254 A. The pH of the slurry was 7.5. After about 1 hour the precipitation was completed.

After washing of the precipitate with approximately 30 liter of cold water, the precursor of the catalyst formed was filtered and dried in an oven at 110° C. The catalyst was activated at 400° C. with hydrogen. TPR peak maximum and the specific pore volume were determined (on calcined precursor) as 385° C. and 0.52 ml/g, respectively.

EXAMPLE 3

37.5 wt. % Ni on Silica 1000 ml of a solution of nickel chloride (71.7 g/l nickel) in water and 750 ml sodium carbonate (220 g/l) solution were simultaneously pumped into a well-stirred 4-liter precipitation vessel at a temperature of 60° C. The starting volume of the water in the precipitation vessel was 2000 ml and contained 100 gram of highly porous silica powder having a specific pore volume of 1.72 ml/g. The pH of the slurry was 7.5 and after about 1 hour the precipitation was completed.

After washing of the precipitate with approximately 30 liter of cold water, the precursor of the catalyst formed was filtered and dried in an oven at 110° C. The catalyst was activated at 400° C. with hydrogen. TPR peak maximum and the specific pore volume were determined (on calcined precursor) as 395° C. and 0.57 ml/g, respectively.

The nickel content of the reduced catalyst was 43.2 wt. %, based on the weight of the catalyst; the amount of nickel reduced was 42.3 wt. %; and the amount of nickel present in metallic form was 97.9 wt. %.

EXAMPLE 4 (REFERENCE)

37.5 wt. % Ni on Silica, with Aging Step at 60° C.

1000 ml of a solution of nickel chloride (71.7 g/l nickel) in water and 750 ml sodium carbonate (220 g/l) solution were simultaneously pumped into a well-stirred 4-liter precipitation vessel at a temperature of 60° C. The starting volume of the water in the precipitation vessel was 2000 ml and contained 100 gram of highly porous silica powder having a specific pore volume of 1.72 ml/g. The pH of the slurry was 7.5 and after about 1 hour the precipitation was completed. After precipitation, the slurry was kept at a hold temperature of 60° C. for 4 hours (aging) and than washed with approximately 30 liter of cold water. The precursor of the catalyst formed was filtered and dried in an oven at 110° C. The catalyst was activated at 400° C. with hydrogen.

The nickel content of the reduced catalyst was 40.5 wt. %, based on the weight of the catalyst; the amount of nickel reduced was 29.7 wt. %; and the amount of nickel present in metallic form was 73.3 wt. %.

Shown below in Table 1 is a comparison of a nickel catalyst prepared with no aging step (Example 3, no hold temperature), and with an aging step (Example 4, hold temperature of 60° C.). IV-70 values were measured. IV-70 is the time that is required to reach an iodine value of 70 using the Activity Test explained below.

TABLE 1

37.5 wt. % Ni on silica, precipitation temperature 60° C.

| Example No. | Hold temp (° C.) | Hold time (h) | TPR peak (° C.) | $N_2$- Specific PV (ml/g) | Average Pore Diameter (Å) | BET-SA (m²/g) | Time to IV-70 (min) |
|---|---|---|---|---|---|---|---|
| 3 | n.a. | — | 395 | 0.57 | 92 | 248 | 27.5 |
| 4 | 60 | 4 | 460 | 0.3 | 35 | 345 | * |

* IV-70 was not reached within an acceptable time. After 60 min hydrogenation time, the IV had dropped to only 100.

Activity Test of the Catalyst:

The activity for soy bean oil hydrogenation, one of the essential features of the catalyst to be used in the present invention, is determined as follows:

In a 1 liter autoclave with a hollow shaft stirrer (Dispersie Max™) and agitation speed of 2000 rpm the activity is determined by hydrogenating 500 g soy bean oil having an iodine value of 128 at 204° C. at a hydrogen pressure of 0.7 bars with an amount of catalyst corresponding to 0.0035 wt. % nickel. The oil is hydrogenated to an iodine value of 70.

The time to IV-70 using the catalysts of Examples 2-4 is compared with that of the reference catalyst (Example 1) under the same conditions, as shown in Table 2. The activity is expressed as the time (min) needed to reach an IV of 70.

As can be seen from the results below, the catalysts of the present invention (Examples 2 and 3) are more effective in the hydrogenation of the soy bean oil. The catalyst corresponding to Example 4 does not have a TPR peak as required by the present invention. Additionally aging at 60° C. for 4 hours has a negative impact on the performance of the catalyst and resulted in a much higher surface area and lower specific pore volume of the catalyst. Without wishing to be bound by theory, it is believed that this is caused by too much nickel-silica interaction.

Preferably, the activity of the catalyst of the invention should be such that the time to IV-70 is less than 35 min, more preferably less than 32 min.

TABLE 2

| Catalyst Example | Time to IV-70 (min) | Activity (%) versus Example 1 (reference) |
|---|---|---|
| Example 1 (reference) | 48.1 | 100 |
| Example 2 | 31.9 | 151 |
| Example 3 | 27.1 | 179 |
| Example 4 (reference) | * | * |

* IV-70 was not reached within an acceptable time. After 60 min hydrogenation time, the IV had dropped to only 100.

With other feedstocks, similar or higher activities were found.

The invention claimed is:

1. Catalyst comprising nickel on a solid silica support, wherein said catalyst has a specific pore volume of at least 0.4 ml/g, a TPR peak maximum within the range of 360-420° C. and wherein said catalyst comprises 20-48 wt. %, of nickel calculated as metallic nickel on the weight of the calcined catalyst.

2. Catalyst according to claim 1, wherein >90 wt. % of the nickel is present in the metallic form.

3. Catalyst according to claim 1, wherein said catalyst has a BET surface area between 160 to 300 $m^2/g$.

4. Catalyst according to claim 1, resulting in an IV-70 of less than 35 minutes.

5. Droplet comprising a reduced catalyst according to claim 1 coated in a fatty substance, wherein said droplet comprises about 9-13 wt. % nickel, calculated as metallic nickel, about 9-26 wt. % $SiO_2$ and the balance of the droplet is the fatty substance.

6. Process for preparing a catalyst according to claim 1, wherein
a nickel source and a solid silica support are mixed in a liquid solution and the nickel is deposited by precipitation onto the solid silica support to form a catalyst precursor at a precipitation temperature of <70° C.,
the catalyst precursor is brought to a temperature of ≤50° C.,
the catalyst precursor is isolated from the solution, and
the catalyst precursor is activated to form the catalyst.

7. Process for preparing a catalyst according to claim 1, wherein
a nickel source and a solid silica support are mixed in a liquid solution and the nickel is deposited by precipitation onto the solid silica support to form a catalyst precursor at a temperature ≤60° C.,
the catalyst precursor is brought to a temperature of ≤50° C.,
the catalyst precursor is isolated from the solution,
the catalyst precursor is activated to form the catalyst,
and wherein the pore structure of the solid silica support is substantially maintained, as reflected in the decrease in the pore volume (in ml/g) from silica support to catalyst precursor, which is less than 80%.

8. Process according to claims 6, wherein the catalyst precursor is aged prior to bringing the temperature ≤50° C. according to the expression $\tau << 10030 \times e^{(-0.135 \times \xi)}$, wherein $\tau$ is the aging time in hours and $\xi$ is the aging temperature in ° C.

9. Process according to claims 6, wherein the precipitation is performed at a pH between 7.0-8.0.

10. Process according to claims 6, wherein the catalyst precursor is activated by reduction with hydrogen at a temperature between 350-450° C.

11. Catalyst, which is obtainable by the process according to claim 6.

12. Process for the hydrogenation of an unsaturated fatty material, preferably an oil or a fatty acid, wherein said unsaturated fatty material is contacted with hydrogen in the presence of the catalyst according to claim 1

13. Process according to claim 12, wherein the hydrogenation is carried out in a fixed bed or slurry process comprising said catalyst.

14. Catalyst according to claim 1, wherein said catalyst is in the form of a shaped catalyst.

15. Catalyst according to claim 14, wherein said catalyst is in the form of an extrudate or a tablet.

16. A fixed bed process comprising using a catalyst according to claim 1, wherein said fixed bed process is selected from the group consisting of dearomatization, desulfurization of petrochemical feedstocks, hydrogenation of petrochemical feedstocks and hydrogenation of functional groups including aldehydes and nitro groups.

* * * * *